United States Patent
Mosher et al.

(10) Patent No.: US 7,316,910 B2
(45) Date of Patent: Jan. 8, 2008

(54) RAPID TEST FOR HEMOLYTIC STREPTOCOCCUS

(75) Inventors: Leroy E. Mosher, Gilsum, NH (US); Craig J. Bell, E. Swanzey, NH (US)

(73) Assignee: Kinase Scientific, LLC, Keene, NH (US)

( * ) Notice: Subject to any disclaimer, the term of this patent is extended or adjusted under 35 U.S.C. 154(b) by 0 days.

(21) Appl. No.: 11/143,234

(22) Filed: Jun. 2, 2005

(65) Prior Publication Data

US 2005/0272113 A1    Dec. 8, 2005

Related U.S. Application Data

(60) Provisional application No. 60/576,448, filed on Jun. 3, 2004.

(51) Int. Cl.
| | |
|---|---|
| *G01N 33/569* | (2006.01) |
| *C12Q 1/00* | (2006.01) |
| *C12Q 1/14* | (2006.01) |
| *C12N 9/70* | (2006.01) |
| *A61K 39/09* | (2006.01) |
| *A61K 38/48* | (2006.01) |
| *A61K 39/00* | (2006.01) |
| *A61K 39/40* | (2006.01) |
| *A01N 63/00* | (2006.01) |

(52) U.S. Cl. ............ 435/7.34; 435/4; 435/36; 435/216; 424/244.1; 424/94.64; 424/184.1; 424/165.1; 424/237.1; 424/93.44

(58) Field of Classification Search ............ 435/7.34, 435/4, 36, 216; 424/94.64, 184.1, 165.1, 424/237.1, 244.1, 93.44
See application file for complete search history.

(56) References Cited

U.S. PATENT DOCUMENTS

| | | | |
|---|---|---|---|
| 4,544,545 A | 10/1985 | Ryan et al. | 424/1.1 |
| 4,863,875 A | 9/1989 | Bailey et al. | 436/518 |
| 5,372,935 A | 12/1994 | Capps | |
| 5,374,538 A | 12/1994 | Bratthall | 435/36 |
| 5,424,193 A | 6/1995 | Pronovost et al. | |
| 5,468,606 A | 11/1995 | Bogart et al. | |
| 5,741,662 A | 4/1998 | Madsen et al. | |
| 5,962,306 A | 10/1999 | Ollar et al. | |
| 6,030,835 A | 2/2000 | Musser et al. | 435/340 |
| 6,251,581 B1 | 6/2001 | Ullman et al. | |
| 6,667,161 B1 | 12/2003 | Johnson et al. | |
| 2005/0069900 A1 | 3/2005 | Lentrichia | |
| 2005/0142622 A1* | 6/2005 | Sanders et al. | 435/7.32 |

OTHER PUBLICATIONS

Unsworth (Hylauronidase production in Streptococcus milleri in relation to infection, J. Clin Pathol, 1989; 42: 506-10).*
Tewodros et al (Streptokinase activity among group A streptococci in relation to streptokinase genotype, plasminogen binding, and disease manifestations, Microbial Pathogenesis, 1995; 18: 53-65).*
Author unknown (patent is in Japanese), Derwent No. 1976-46918X.*
Benchetrit et al (Hyaluronidase production by groups A, B, C, and G streptococci: A statistical analysis, Zentralbl Bakteriol Mikrobiol Hyg, 1994; 257(1): 27-37).*
Unsworth (Hylauronidase production in Streptococcus milleri in relation to infection, J. Clin Pathol, 1989; 42: 506-10).*
Jackson et al (Streptokinase and Staphylokinase, Methods in Enzymology, 1981; 80: 387-394.*
A. Heath et al., Infections Immunity 67 (1999): 5298-5305, 67(10).
Castellino et al. "Human Plasminogen" Methods in Enzymology, vol. 80, pp. 365-378 (1981).
Streptococcal Skin Infections from www.kcom.edu/faculty/chamberlain/Website/lectures/tritzid/strpskn.htm, 4 pages total.
Palmer et al. Assembly mechanism of the oligomeric streptolysin O pore: the early membrane lesion is lined by a free edge . . . The EMBO Journal 1998, vol. 17, pp. 1598-1605.
Tricot et al. Collection, Tumor Contamination, and Engraftment Kinetics of Highly Purified Hematopoietic Progenitor . . . Blood Jun. 15, 1998, vol. 91, No. 12, pp. 4489-4495.
Steiner et al. Dual Control of Streptokinase and Streptolysin S Production by the covRS and fasCAX . . . Infection and Immunity Jul. 2002, vol. 70, No. 7, pp. 3627-3636.
Streptococcus pyogenes from Todar's Online Textbook of Bacteriology (c) 2002 Kenneth Todar University of Wisconsin-Madison Department of Bacteriology, Introduction—1 page total.
The Product Yellow Alert Non-Specific Rapid Strep Indicator (undated).

* cited by examiner

Primary Examiner—Robert A. Zeman
Assistant Examiner—Lakia J Tongue
(74) Attorney, Agent, or Firm—Gifford, Krass et al.

(57) ABSTRACT

A reagent for the detection of an extracellular enzymatically active protein produced by a beta-hemolytic streptococcus bacteria found in a host biological fluid includes a proteinaceous substrate or a cholesterol-containing membrane substrate for the extracellular protein. The substrate is nonspecific within the groups of beta-hemolytic streptococcus bacterium and is in contact with an inert solid matrix. Upon reaction between the streptococcus enzymatically activate protein and the substrate, a color change discernable by an unaided human eye results. Extracellular streptococcus protein found in saliva represents a less invasive source of biological fluid for the determination as to whether a host suffers acute pharyngitis.

11 Claims, 6 Drawing Sheets

RAPID TEST FOR HEMOLYTIC STREPTOCOCCUS

RELATED APPLICATION

This application claims priority of U.S. Provisional Patent Application Ser. No. 60/576,448 filed Jun. 3, 2004, which is incorporated herein by reference.

FIELD OF THE INVENTION

The present invention in general relates to diagnostic testing for the presence of a microbe in a biological sample, and in particular to a nonspecific rapid test for the presence of streptococcal bacteria normally associated with the production of streptokinase.

BACKGROUND OF THE INVENTION

Strep throat is an infection of the pharynx caused by the bacteria *Streptococcus pyogenes*. The pharynx is the part of the throat between the tonsils and the larynx, or voice box. The main pathogenic strep groups for humans are A, B, C, D and G. More than 90% of streptococcal disease in humans is caused by Group A beta-hemolytic strep (GABHS).

*Streptococcus pyogenes* is the bacterium cause of several human infections including acute pharyngitis, impetigo, acute rheumatic fever, scarlet fever, and toxic shock syndrome. The particular bacterium associated with these diseases are beta-hemolytic streptococci (BHS) of Groups A, B, C and G, of which Group A is the most dominant pathogen.

The bacteria that cause streptococcal infection such as strep throat emits toxins that result in inflammation. The predominant locale of the infection is the pharyngeal mucosa. These toxins are central in facilitating the progression of the infection. Symptoms of strep throat include a sore throat that starts suddenly, without runny nose or congestion. The throat is extremely red, and swallowing is painful. White patches typically appear on the tonsils, and lymph nodes in the neck swell. Symptoms may also include fever, headache, loss of appetite and fatigue. Children with strep throat may also exhibit nausea, vomiting and abdominal distress.

Existing methodologies for determining when severe sore throat symptoms may be a strep infection, such as GABHS, require a visit to a physician's office. The most commonly used test is an antigen-based test, specific to GABHS. These rapid strep tests require a deep swab sample of the mucus in the pharyngeal area, which is prepared using one or two reagent chemicals. The test is considered adequate for Strep A (GABHS) positive readings, and takes about 3-15 minutes. When a negative rapid strep test occurs, it is common practice to perform a laboratory cell culture to confirm or rule out the presence of a Strep A infection. The culture is required owing to a high incidence of false negatives associated with the antigen specificity of current tests. Exemplary of these tests are those disclosed in U.S. Pat. Nos. 4,863,875; 5,374,538 and 6,030,835.

People who may be at risk for serious complications from strep infection include people who have chronic conditions such as diabetes, weakened immune systems or immunodeficiency disorders. Serious complications from untreated strep infection include otitis media, peritonsillar abscesses, meningitis, peritonitis, scarlet fever and rheumatic fever. Prompt diagnosis and treatment with antibiotics are the best ways to prevent infection spread and complications.

The current rapid tests require swabbing the back of the throat to obtain a mucus sample and transferring the sample to a container or test paper. The swabbing of the throat represents a traumatic event for a patient, as well as the healthcare worker. The collection of a throat swab is made all the more difficult with pediatric patients who represent a strep-vulnerable population. The addition of two or more reagents is required before a visual check for the development of a color indicator. The color development is a result of GABHS antigens reacting with the antibodies introduced by the test. The methodology is sufficiently complicated to require a laboratory technician to properly perform the test.

Thus, there exists a need for a non-antigen specific rapid test for the presence of beta-hemolytic streptococcus in a bodily fluid that is operative independent of a mucosal swab. Additionally, there exists a need for a rapid beta-hemolytic streptococcus test that is amenable to home use as a pre-screen for consultation with a health professional.

SUMMARY OF THE INVENTION

A reagent for the detection of an extracellular protein produced by a beta-hemolytic streptococcus bacteria found in a host biological fluid includes a proteinaceous substrate or a cholesterol-containing membrane substrate for the extracellular protein. The substrate is nonspecific within the groups of beta-hemolytic streptococcus bacterium and is in contact with an inert solid matrix. Upon reaction between the streptococcus enzymatically activate protein and the substrate, a color change is discerned. Extracellular streptococcus protein found in saliva represents a less invasive source of biological fluid for the determination as to whether a host suffers acute pharyngitis or tonsillitis.

A process for detecting a beta-hemolytic streptococcus bacterium in a host includes collecting a biological fluid from the host where saliva, as compared to pharyngeal mucus, is a preferred biological fluid. The biological fluid includes beta-hemolytic streptococcus extracellular enzymatically active protein. The saliva or other biological fluid is contacted with a chromogenic substrate for the beta-hemolytic streptococcus protein. Observation of a color change associated with streptococcus protein cleaving a proteinaceous substrate, or in the case of a cholesterol-containing membrane creating pores therein, creates a color change discernable by an unaided human eye.

A kit for detection of beta-hemolytic streptococcus bacterium in a host includes a proteinaceous substrate or a cholesterol-containing membrane susceptible to the action of an extracellular protein produced by beta-hemolytic streptococcus that upon reaction yields a color change discernable by an unaided human eye. An applicator for collecting a bodily fluid from a host harboring the beta-hemolytic streptococcus is provided along with instructions for the use of the kit for rapid identification of beta-hemolytic streptococcus.

BRIEF DESCRIPTION OF THE DRAWING

The current invention is described in further detail in conjunction with the following referenced drawings.

DETAILED DESCRIPTION OF THE INVENTION

Figure 1B:
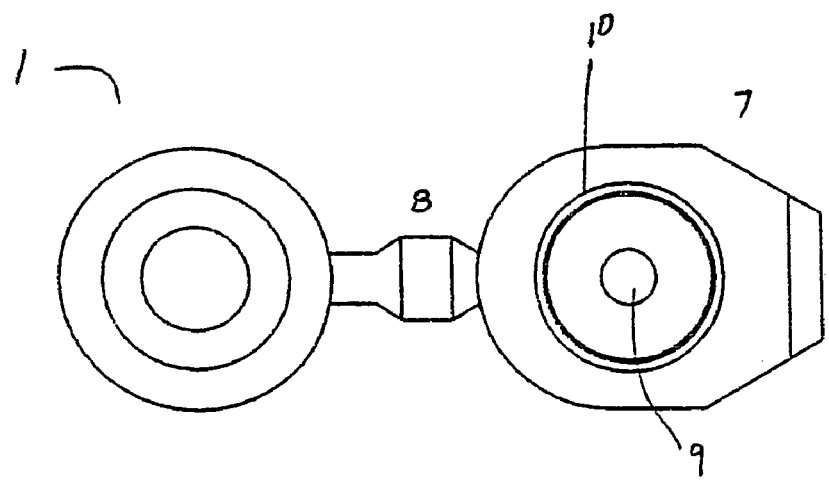
FIG. 1B is a top view of the container.

The present invention has utility as a procedurally simple test to determine the presence of a beta-hemolytic streptococcal bacteria (BHS) in a host. Unlike the majority of BHS tests that rely on antigen-specific binding to an antibody or fragment thereof to confer specificity as to the group and strain of BHS, the present invention provides a simple indication of a generic BHS bacterial population being present.

As used herein "beta-hemolytic streptococcus" is defined to include those groups *Streptococcus pyogenes* that are pathogenic through production of at least one extracellular enzymatically active protein, streptokinase, streptolysin, streptodomase, hyaluronidase, or cysteine proteinase. These groups specifically include A, B, C and G. It is appreciated that hyaluronidase and cysteine proteinase are also excreted by other organisms. Specifically, *P. gingivalis* produces arginine specific cysteine proteinase. Nonetheless, detection of these proteins in combination with BHS specific proteins adds to the certainty of the result.

The present invention provides a rapid detection kit for beta-hemolytic streptococcus bacteria through the reaction of an extracellular protein produced by BHS with a proteinaceous substrate or a cholesterol-containing membrane to induce a color change discernable by an unaided human eye. Suitable substrates include oligopeptide p-nitroanilides that are cleaved by the BHS extracellular protein directly or through activation of a secondary enzyme.

Streptokinase and cysteine proteinase are representative of the extracellular BHS proteins effective to cleave a proteinaceous substrate. Additionally, it is appreciated that streptolysin that is produced by BHS is an exotoxin that binds to cell membranes containing cholesterol. Streptolysin thereafter oligomerizes to form large pores in the cell membrane that effectively lyse the membrane. As a result of streptolysin action, red blood cells represent a chromogenic substrate for streptolysin. In addition, it is appreciated that a synthetic membrane containing cholesterol is readily formed that encompasses a dye species that changes appearance to the unaided eye upon the lysis of the synthetic membrane. U.S. Pat. No. 4,544,545 teaches the formation of such a lipid bilayer.

In a preferred embodiment, streptokinase acts on lysine-plasminogen to convert this substrate to an active enzyme, plasmin. Plasmin in turn reacts with an oligopeptide p-nitroanilide to free a yellow-colored aniline dye. Substrates for plasmin, streptokinase-plasmin, or a streptokinase-plasminogen complex include commercially available substrates S-2251 (D-Val-Leu-Lys-p-Nitroanilide Dichloride), S-2403 (pyroGlu-Phe-Lys-p-Nitroanilide Hydrochloride), S-2406 (pyroGlu-Leu-Lys-p-Nitroanilide Hydrochloride) and combinations thereof. It is appreciated that these are representative chromogenic substrates for streptokinase and that other substrates such as chemiluminescent, fluorogenic and other chromogenic oligopeptide substrates are operative in place of, or in combination with, the aforementioned nitroanilide oligopeptides. Streptokinase activity has previously been measured chromogenically. W. Tewodros et al., *Microbiology Pathology* 18 (1995): 53-65.

BHS cysteine proteinase is also noted to be specific towards the chromogenic oligopeptide substrate N-succinyl Phe-Ala-p-Nitroanilide and Leu-p-Nitroanilide. It is appreciated that substrates for both streptokinase and cysteine proteinase are readily included within the inventive test kit in which greater sensitivity to the presence of BHS is desired.

An additional substrate operative for the detection of BHS is a membrane having cholesterol within the membrane and containing within the membrane volume a chromophore that changes color upon membrane lysis through oligomerization of streptolysin O or S. Membranes including cholesterol that are suitable as substrates for detection of BHS streptolysin include red blood cells and lipid bilayers including cholesterol and chromophores. The chromophores illustratively include hemoglobin and the aforementioned nitroanilide oligopeptides. It is appreciated that as with streptokinase substrates, cysteine proteinase and streptolysin substrates are readily provided that include a chemiluminescent, fluorogenic or other chromogenic species therein. Such chemiluminescent and fluorogenic species couplable to oligopeptides are insertable into liposomal membranes are well known to the art and are described in U.S. Pat. No. 4,544,545. Streptolysin S activity alone or in combination with streptolysin O activity has also previously been measured chromogenically. A. Heath et al., *Infectious Immunity* 67 (1999): 5298-5305.

Preferably, a proteinaceous substrate or cholesterol-containing membrane bounding a chromophore are provided within an inert solid matrix. Suitable materials for the formation of an inert solid matrix include cellulosic materials such as filter paper, natural fibers such as cotton, linen, silk, and wool; nitrocelluloses, carboxyalkyl celluloses, synthetic polymer fabrics such as polyamides, polylactic acids, polyacrylics and sintered polyalkylene beads.

Alternatively, solution-based substrates and/or membranes for BHS extracellular proteins are provided in conventional buffer solutions such as PBS (phosphate buffered saline). Preferably, a buffer solution includes an antimicrobial agent to preclude substrate degradation by opportunistic microorganisms. It is further appreciated that the shelf life of an inventive reagent and therefore a kit for performing an inventive nonspecific BHS strep test is increased by storing the reagent under cool conditions such as those found in a consumer refrigerator freezer. In instances where proteinaceous substrates or cholesterol-containing membranes are in solution form, or red blood cells are provided as a substrate for streptolysin, preferably a cryopreservative is present. Typical of cryopreservative solutions are those that include 2% heta starch, 4% albumin and 7.5% dimethylsulfoxide.

Biological fluids from a host suitable for detection of BHS therein include sweat, mucosa, saliva, blood, tears, and pus. In a circumstance where one is attempting to detect BHS associated with a sore throat, the preferred biological fluid is saliva, in contrast to prior art antigenic binding that has required throat mucosa. The present invention is based upon the recognition that saliva of an individual having a BHS-induced pharyngitis contains streptokinase, streptolysin, cysteine proteinases and other exotoxins associated with BBS. It is appreciated that a uterine swab is suitable for detecting puerperal fever or the presence of BHS in the birth canal prior to the initiation of delivery. Additionally, seepage from a wound in the form of plasma, blood, and/or pus is readily evaluated by an inventive test for BHS.

Referring now to the figures, exemplary embodiments of the present invention are provided. Referring now to the embodiment of the invention shown in FIG. 1A and FIG. 1B, a container is shown generally at 1 in FIGS. 1A and 1B. The container 1 is preferably injection molded thermoplastic illustratively including polypropylene and styrene. The container 1 has an inner surface 2 and an outer surface 3 that defines a wall 4. The container 1 has at least one open end 5 and bottom well 6. The container 1 has cap 7 attached for convenience by a living hinge strap 8. Cap 7 has a through hole 9 and snap closure ring 10. When cap 7 is inserted into container open end 5, snap closure ring 10 engages with undercut 11. The container 1 is optionally molded with stand 12 to allow the container to stand upright on a flat surface. An inventive BHS reagent formula 13 is located in the bottom well 6.

The reagent formula 13 is typically dispensed into the container 1 by a manual pipette, automated pipette, or other precision dispensing means currently known in the art. The volume of reagent formula 13 disposed is between 5 and 500 microliters. The indicating formula is then dried at room temperature or at an elevated temperature that does not denature the formula. Reagent formula 13 is reactive with a BHS extracellular protein. Preferably, the BHS protein includes at least one of streptokinase, streptolysin O, streptolysin S, and cysteine proteinase. Preferably, the reagent chromogenically detects at least streptokinase. A reagent formula for streptokinase includes a chromogenic substrate D-Val-Leu-Lys-p-Nitroanilide Dihydrochloride (Sigma) and the single chain glycoprotein plasminogen (Sigma), which is the inactive precursor to the active enzyme plasmin. The plasmin is isolated from a variety of sources. Human plasminogen is obtained from pooled plasma, glu-plasminogen, lys-plasminogen, recombinant, and/or fractions of plasminogen.

Figure 2:
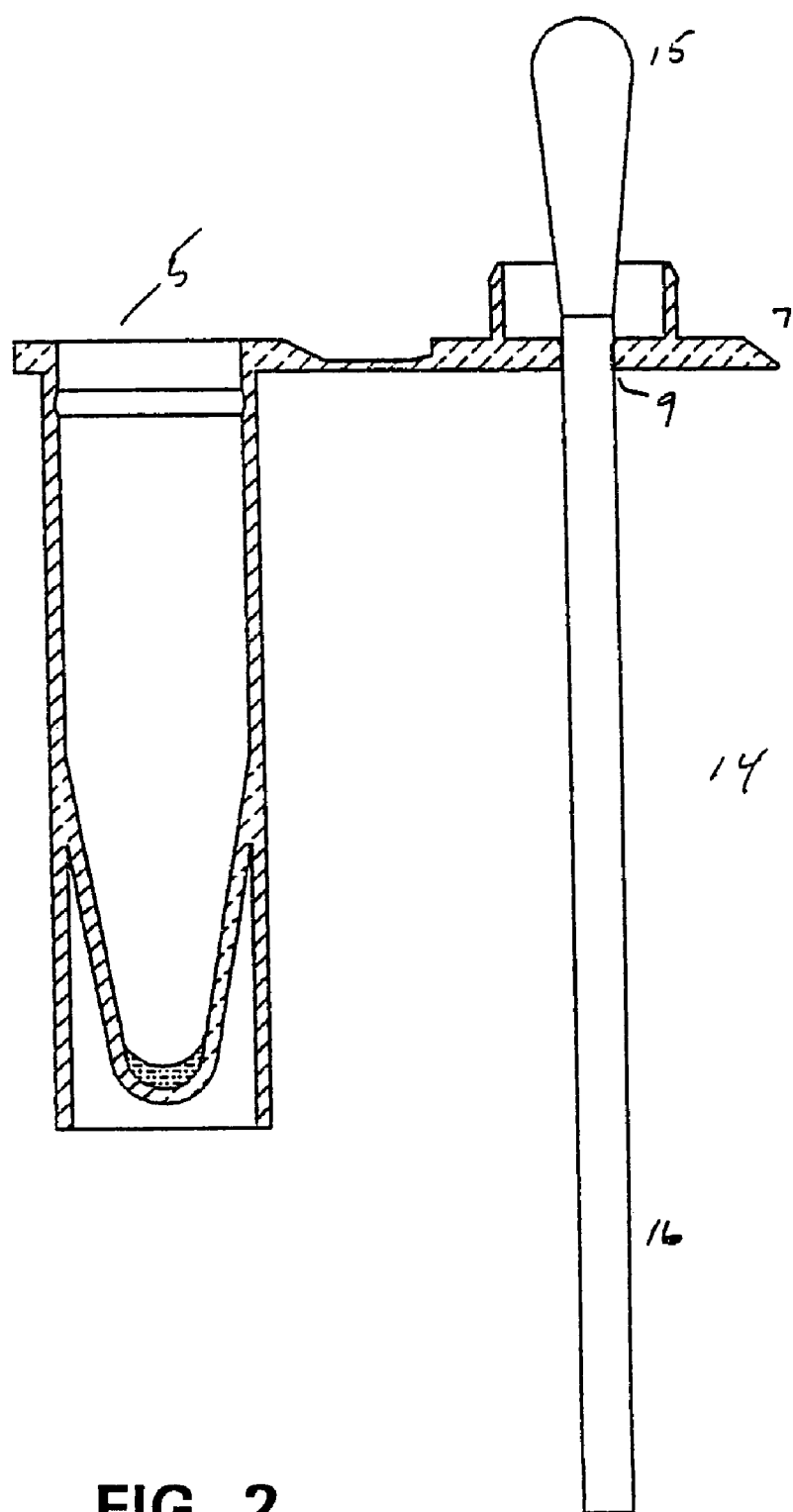
FIG. 2 shows the initial position of the swab in the cap of the container.

Referring to FIG. 2, a swab 14 is used to obtain a biological sample. The container 1 is shown with fiber tipped swab 14 placed with shaft 16 through hole 9 in cap 7. The tip 15 is positioned close to cap 7 so that cap 7 with swab 14 in place can be closed without touching tip 15 on the container opening.

It is appreciated that inventive test kits for detecting BHS in biological fluids other than saliva optionally vary in host sample aliquot volumes and reagent quantity to attain desired levels of sensitivity and specificity. Factors to achieve these variations include the design of the sampling swab, type of material, and shaft design where hollow plastic shafts increase the sample volume by wicking liquid by capillary action. Preferably a swab collects enough biological fluid to hydrate the indicating formula. It is appreciated that excessive liquid will dilute the reagent formula and result in a less intense chromogenic reaction.

Figure 1A:
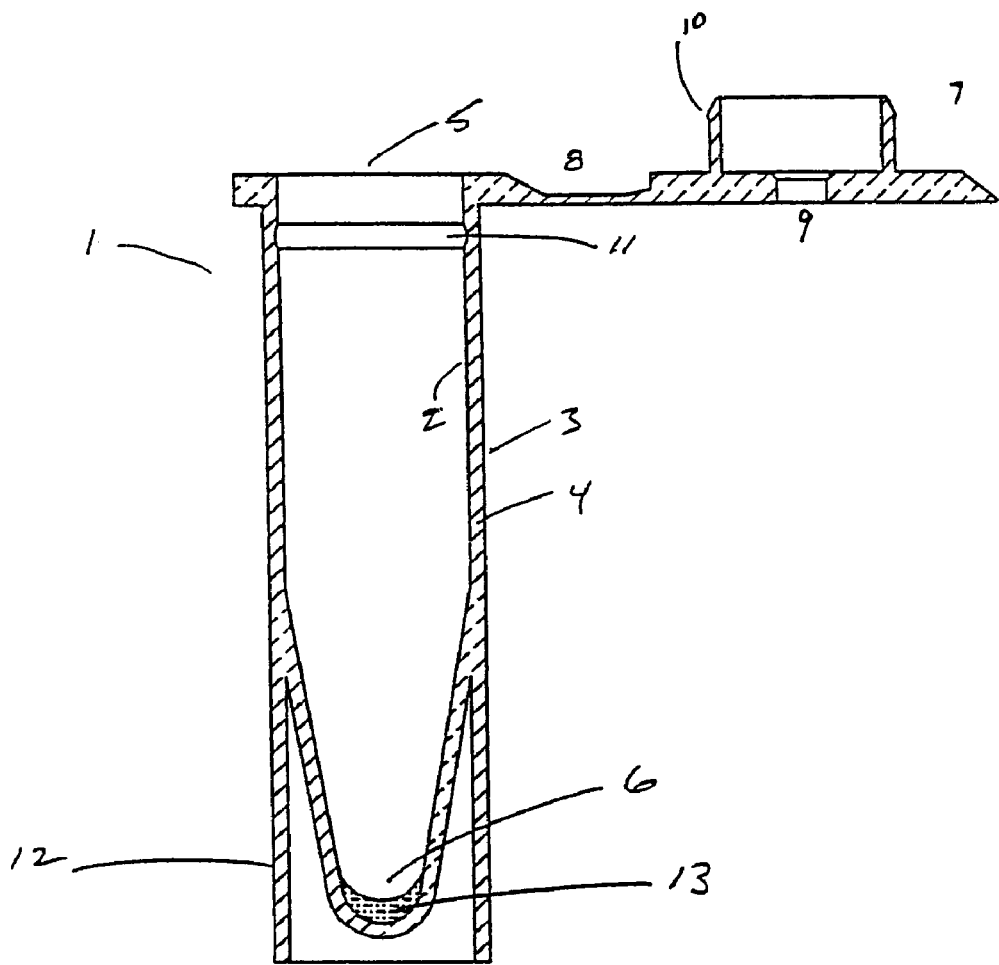
FIG. 1A is a cross section view of the container with the indicating formula in the well.
Figure 3A:
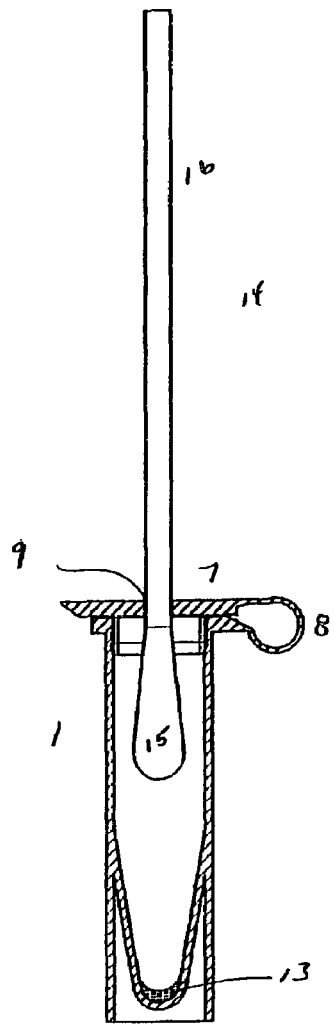
FIG. 3A shows the container cap closed with the swab in its initial position.
Figure 3B:
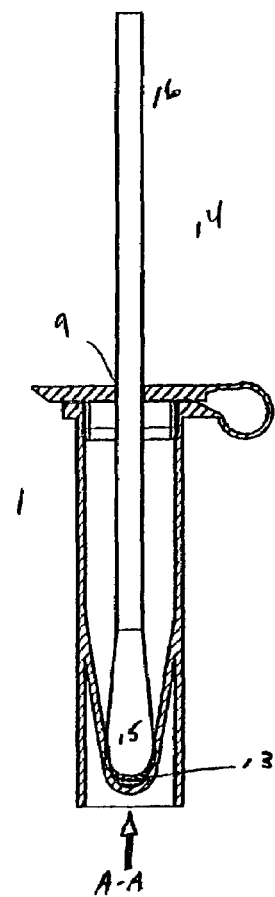
FIG. 3B shows the container cap closed with the swab in its final position.

FIG. 3A shows the container 1 with cap 7 snapped closed, engaging snap ring 10 and undercut 11, where like numerals correspond to those used with respect to FIGS. 1A and 1B. Hinge 8 is shown in its hinged/flexed position and swab 14 in its initial position in cap 7. FIG. 3B shows closed container 1 with swab 14 slid so tip 15 is in contact with indicating formula 13. Swab 14 is advanced by pushing shaft 16 through hole 9 until tip 15 is stopped by bottom well 6. To enhance the contact and mixing of the biological sample contained on tip 15 and reagent formula 13, the shaft 16 is optionally rotated while applying downward pressure. The color change typically occurs between 1 and 30 minutes after contact between the fluid and the reagent formula 13 and is viewed in the direction shown in FIG. 3B as arrow A-A.

It is appreciated that a reagent formula can include in a single volume proteinaceous substrates for streptokinase and cysteine proteinase alone, or in combination with a cholesterol-containing membrane reactive towards streptolysin. Alternatively, the use of two or more separate reagent formulas each specific for a different BHS exotoxin affords greater selectivity to BHS since the possibility of contamination with a biological fluid with two or more of the exotoxins produced by BHS or a false positive becomes much less likely. It is appreciated that the multiple separate reagent formula kit containing two or more containers 1, each specific to a different BHS exotoxin, necessarily increases the cost of the resulting kit and the possibility of multiple swabs. Additionally, while in a preferred embodiment streptokinase is detected through interaction with plasminogen introduced into a reagent formula, it is appreciated that a simplified streptokinase reagent formula is operative that relies on the presence of plasminogen naturally found in the biological fluid and in such an instance, the inventive reagent formula need only include a chromogenic oligopeptide that is a substrate for the streptokinase-plasminogen complex, streptokinase-plasmin complex or plasmin to yield a color change discernable to an unaided human eye. It is appreciated that an inventive reagent formula is readily made of various concentrations of chromogenic substrate or cholesterol containing membrane containing a chromophore to yield different formula sensitivities, color development intensities, and color development times. A starting point for the concentrations is to make a chromogenic substrate concentration of 1 mg/ml and in the case of streptokinase detection, a plasminogen concentration of 400 ug/ml. 10 microliters of each solution alone, or in combination with a like amount of plasminogen solution, is placed into container 1 and let dry at room temperature for streptokinase detection. Streptokinase, streptolysin and cysteine proteinase are typically well visualized at levels of 1 to 1000 nanograms chromophore when the fluid sample is between 0.05 to 1 ml.

An inventive kit to detect the presence of BHS includes a container 1 with the dried reagent formula 13. Preferably, the container is packaged into a foil pouch to protect it from environmental factors such as high humidity and light. More preferably, shelf life is enhanced by keeping the reagent formula in a freezer. The fiber tipped swab 14 can be purchased packaged and sterile from several current manufacturers including Puritan (Guilford, Me.).

Figure 4:
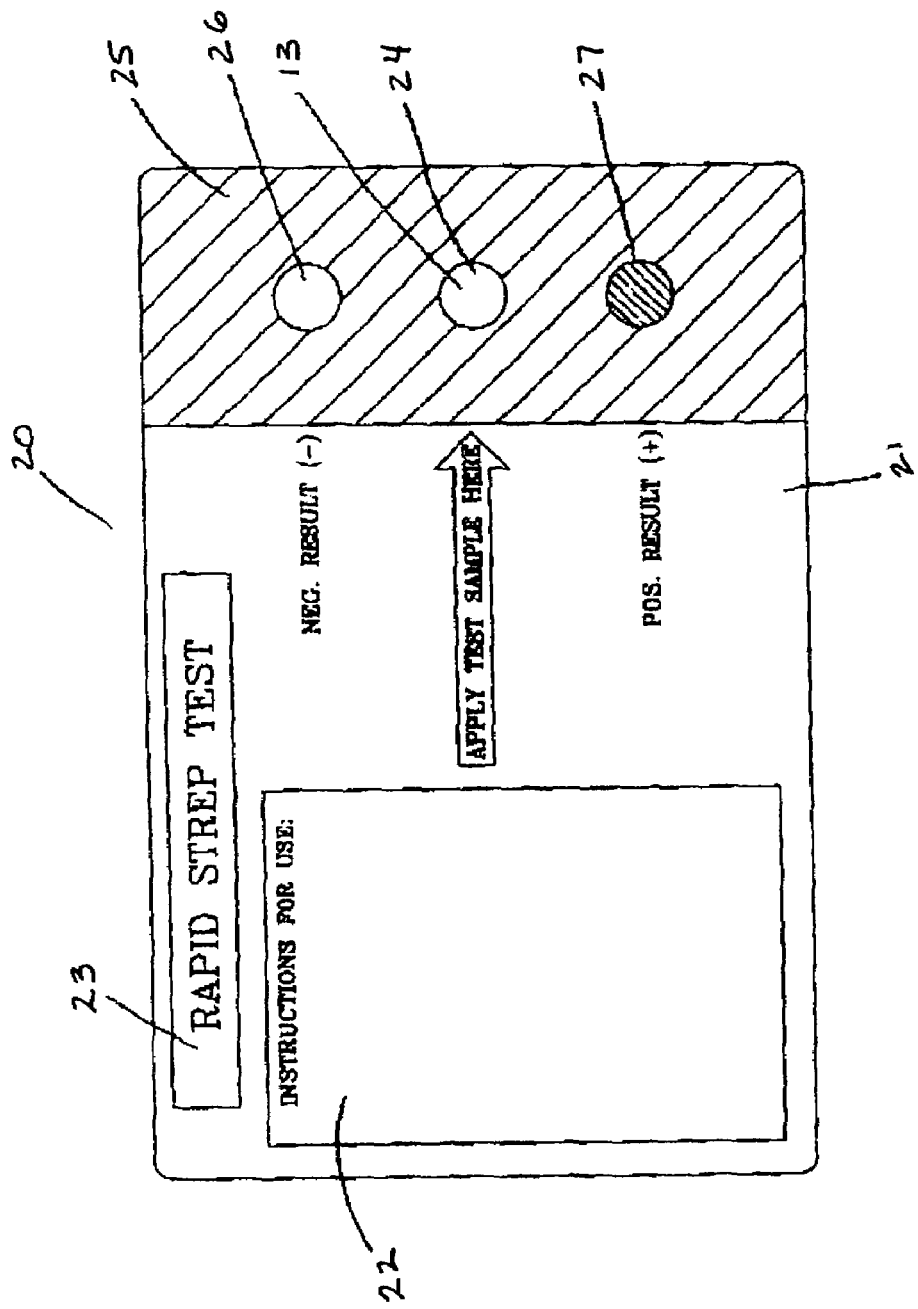
FIG. 4 shows the front view of treated filter paper on a card.

FIG. 4 shows a card format test generally at 20. A card 21 is made of plastic illustratively including high impact polystyrene or a chipboard material. The card 21 is optionally preprinted as shown with information like instructions for use 22 and product name 23. Filter paper 24 illustratively including Schleicher & Schuell 903 Specimen Collection Paper treated with dried reagent formula 13 is provided. The reagent formula 13 is that discussed with regard to FIGS. 1-3. The filter paper 24 is optionally placed on contrasting background color 25, color such as blue or purple to contrast a positive assay result of yellow. Representative color results are optionally printed on card 21 to show negative assay result 26, white, and positive assay results 27, yellow.

Figure 5A:
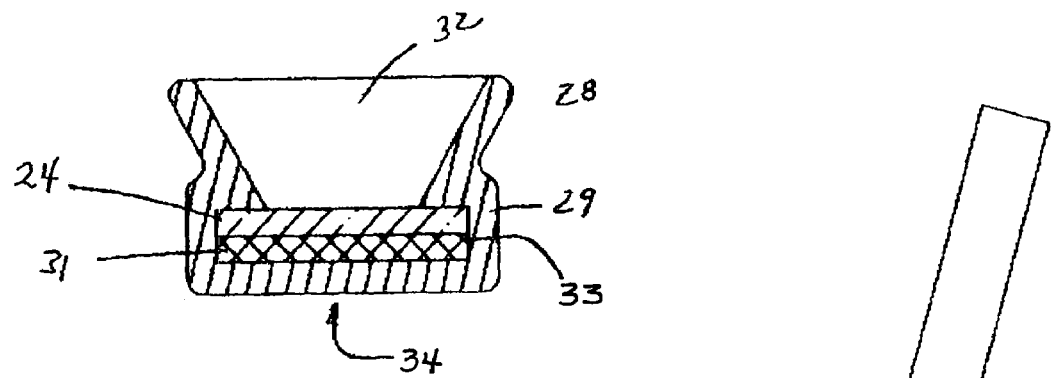
FIGS. 5A and 5B show a cross-section view of test chamber assembly.
Figure 5B:
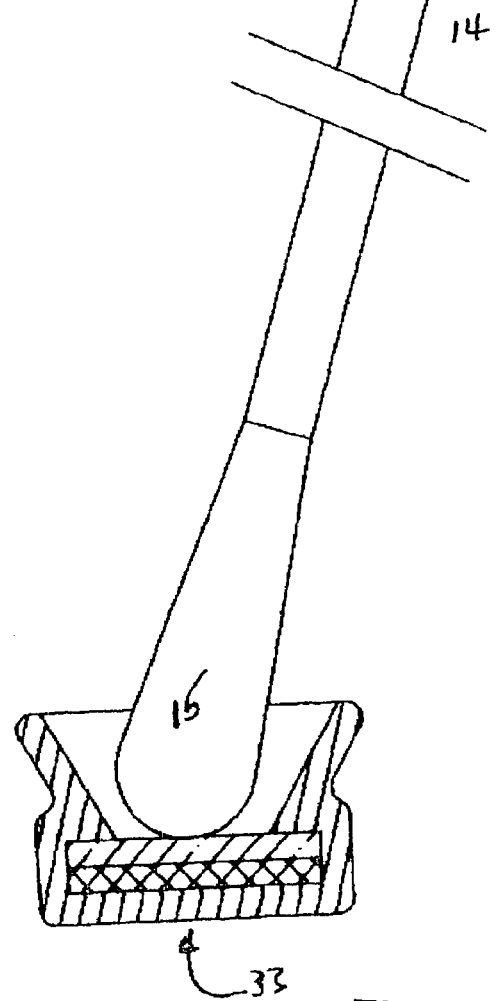

FIGS. 5A and 5B show a cross-section view of test chamber assembly generally at 28. Test chamber assembly 28 is comprised of plastic housing 29. The plastic housing 29 has a space 33 to receive and house one or more treated filter paper components 24, as described with respect to FIG. 4, an opening 32 to allow the host biological fluid to be delivered, and a viewing surface 34. In an embodiment where BHS streptokinase is being detected, filter papers 24 and 31 are located in space 33, with filter paper 24 previously treated with plasminogen and filter paper 31 previously treated with the chromogenic proteinaceous substrate. Filter papers 24 and 31 have a white color. It is appreciated that a test chamber assembly 28 is amenable to mounting in a presentation-like card 21 of FIG. 4.

A fiber tip swab 14, with host biological fluid on tip 15, is brought into contact with filter paper 24 through opening 32. Filter paper 24 wicks the fluid from tip 15. If the fluid contains streptokinase, the plasminogen in filter paper 24 is converted to streptokinase-plasminogen, streptokinase-plasmin, and/or free plasmin. The fluid wicked from filter paper 24 into filter paper 31 cleaves proteinaceous substrate chromophores originally in paper 31, yielding a yellow color observable through viewing surface 33. Filter paper 31 changing from a white color to some portion containing yellow color indicates the presence of the extracellular protein streptokinase, with a BHS population in the host fluid.

Figure 6B:
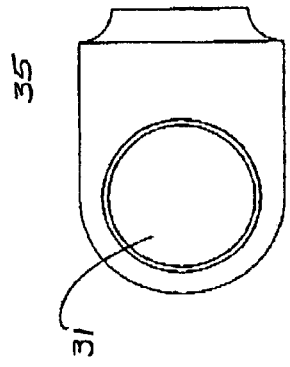
FIGS. 6A and 6B are top views of a hinged treated filter paper assembly.
Figure 7B:
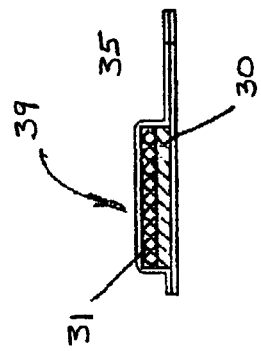
FIGS. 7A and 7B are side views of a hinged treated filter paper assembly.
Figure 6A:
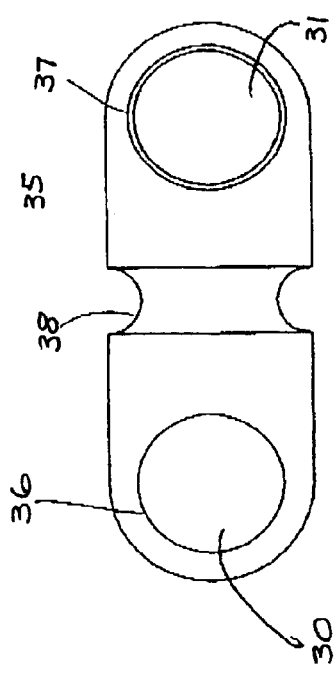
Figure 7A:
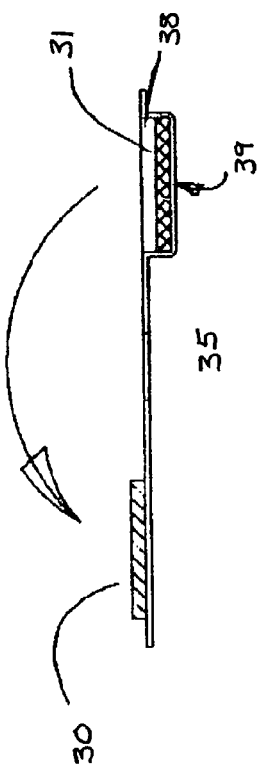

Another filter paper carrier test kit for the reagent formula is shown in FIGS. 6-7 for streptokinase detection. It is appreciated that inclusion of a different reagent formula and the optional removal to the uppermost filter paper layer impregnated with streptokinase allows for the detection of other BHS exotoxins. FIG. 6A shows a top view of a hinged treated filter paper assembly generally at 35. The hinged assembly 35 has a living hinge 38, surface 36 with filter 31, and surface 37 with filter paper 31. FIG. 7A shows a cross-section of a hinged treated filter paper assembly 35. Filter paper 24, as described with respect to FIG. 4, previously treated with plasminogen and filter paper 31 previously treated with a chromogenic substrate are shown. The test sample, not shown, is applied to filter paper 24 and if the liquid sample contains streptokinase the plasminogen in filter paper 24 is converted to streptokinase-plasminogen, streptokinase-plasmin, and/or free plasmin. The hinged assembly 35 is now folded to bring surface 37 and filter paper 31, which has been previously treated with chromogenic substrate, in contact with surface 36 and filter paper 30, now containing the liquid test sample. Sample paper 24 fits into pocket 38 when hinge assembly is folded.

FIG. 6B shows a top view of hinged assembly 35 in its folded position with view of filter paper 31. FIG. 7B shows a cross-section view of hinged assembly 35 in its folded position. The fluid is wicked from filter paper 24 into filter paper 31 containing a chromogenic substrate. The fluid contains streptokinase-plasminogen, streptokinase-plasmin, and/or free plasmin, which cleaves chromophores from the substrate, yielding a yellow color observable through viewing surface 39. Filter paper 31 changing from a white color to some portion containing yellow color indicates the presence of the extracellular protein streptokinase associated with a BHS population in the host fluid.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for detecting streptokinase produced by a beta-hemolytic streptococcus bacterium in a host consisting of:
    collecting a biological fluid sample from the host, said biological fluid sample containing host plasminogen and the streptokinase;
    contacting said biological fluid sample with a first reagent comprising a proteinaceous substrate for an active enzyme, said active enzyme being selected from the group consisting of streptokinase-plasminogen complex, streptokinase-plasmin, and plasmin;
    discerning a color change after the contacting step, to indicate the streptokinase is present in the host, the color change being due to said proteinaceous substrate being cleaved by the active enzyme to yield a colored dye; and
    optionally introducing plasminogen to said fluid in a reagent formula.

2. The process of claim 1 wherein said biological fluid sample is saliva.

3. The process of claim 1 wherein collection of said biological fluid sample involves swabbing said biological fluid sample from the host.

4. The process of claim 3 wherein swabbing is performed orally.

5. The process of claim 3 wherein swabbing is performed vaginally.

6. The process of claim 3 wherein swabbing is performed intralesionally.

7. The process of claim 1 wherein the color change involves a p-nitroanilide substrate for the active enzyme.

8. A process for detecting streptokinase produced by a beta-hemolytic streptococcus bacterium in a host consisting of:
    collecting a biological fluid sample from the host, said biological fluid sample containing host plasminogen and the streptokinase;
    contacting said biological fluid sample with a first reagent comprising a proteinaceous substrate for an active enzyme selected from the group consisting of: streptokinase-plasminogen complex, streptokinase-plasmin, and plasmin;
    discerning a color change after the contacting step, to indicate the streptokinase is present in the host, the color change being due to said proteinaceous substrate being cleaved by the active enzyme to yield a colored dye;
    wherein said substrate is disposed on an inert solid matrix; and
    optionally introducing plasminogen to said fluid in a regent formula.

9. The process of claim 8 wherein said biological fluid sample is saliva.

10. The process of claim 8 wherein the color change involves cleavage of a p-nitroanilide substrate for the active enzyme to yield said colored dye.

11. A process for detecting streptokinase produced by a beta hemolytic streptococcus bacterium in a host consisting of:
    collecting a biological fluid sample from the host, said biological fluid sample containing host plasminogen and the streptokinase;

contacting said biological fluid sample with a first reagent comprising a proteinaceous substrate for an active enzyme, said active enzyme being selected from the group consisting of streptokinase-plasminogen complex, streptokinase-plasmin, and plasmin;

discerning a color change after the contacting step, to indicate the streptokinase is present in the host, the color change being due to said substrate being cleaved by the active enzyme to yield a colored dye;

optionally introducing plasminogen to said fluid in a reagent formula; and optionally contacting a portion of said biological fluid sample to unexposed said first reagent to a second reagent reactive towards a second extracellular protein produced by the beta-hemolytic streptococcus bacterium selected from the group consisting of: streptolysin O, streptolysin S, streptodornase, and cysteine proteinase and discerning a second color change due to reaction between said second reagent and said second extracellular protein.

* * * * *

UNITED STATES PATENT AND TRADEMARK OFFICE
CERTIFICATE OF CORRECTION

PATENT NO. : 7,316,910 B2
APPLICATION NO. : 11/143234
DATED : January 8, 2008
INVENTOR(S) : Leroy E. Mosher et al.

It is certified that error appears in the above-identified patent and that said Letters Patent is hereby corrected as shown below:

Column 8, Line 56, replace "regent" with --reagent--

Column 5, Line 33, replace "plasmin" with --plasminogen--

Signed and Sealed this

Twentieth Day of May, 2008

JON W. DUDAS
*Director of the United States Patent and Trademark Office*